United States Patent
Beke et al.

(10) Patent No.: US 9,452,142 B2
(45) Date of Patent: Sep. 27, 2016

(54) CALCIUM SUPPLEMENT

(71) Applicants: Pradnya Beke, Morristown, NJ (US); Ashish Patel, West Orange, NJ (US); Stephanie Petaway-Hickson, Morris Plains, NJ (US)

(72) Inventors: Pradnya Beke, Morristown, NJ (US); Ashish Patel, West Orange, NJ (US); Stephanie Petaway-Hickson, Morris Plains, NJ (US)

(73) Assignee: Bayer HealthCare LLC, Morristown, NJ (US)

( * ) Notice: Subject to any disclaimer, the term of this patent is extended or adjusted under 35 U.S.C. 154(b) by 0 days.

(21) Appl. No.: 14/272,493

(22) Filed: May 7, 2014

(65) Prior Publication Data

US 2014/0242160 A1 Aug. 28, 2014

Related U.S. Application Data

(63) Continuation of application No. 14/007,569, filed as application No. PCT/US2012/000157 on Mar. 23, 2012, now abandoned, which is a continuation of application No. 13/065,643, filed on Mar. 25, 2011, now abandoned.

(51) Int. Cl.

| | |
|---|---|
| *A61K 33/06* | (2006.01) |
| *A61K 33/10* | (2006.01) |
| *A61K 9/48* | (2006.01) |
| *A61K 9/20* | (2006.01) |
| *A61K 31/194* | (2006.01) |

(52) U.S. Cl.
CPC .......... *A61K 9/4866* (2013.01); *A61K 9/2054* (2013.01); *A61K 31/194* (2013.01); *A61K 33/06* (2013.01); *A61K 33/10* (2013.01)

(58) Field of Classification Search
None
See application file for complete search history.

(56) References Cited

U.S. PATENT DOCUMENTS

| | | | |
|---|---|---|---|
| 4,571,333 A | 2/1986 | Hsiao et al. | |
| 4,772,467 A | 9/1988 | Pak | |
| 4,784,858 A | 11/1988 | Ventouras | |
| 5,762,962 A * | 6/1998 | Georgiades et al. | 424/466 |
| 5,811,126 A | 9/1998 | Krishnamurthy | |
| 5,919,491 A * | 7/1999 | Adusumilli et al. | 424/678 |
| 5,965,163 A | 10/1999 | Miller et al. | |
| 6,090,411 A | 7/2000 | Pillay et al. | |
| 6,887,492 B2 | 5/2005 | Kay et al. | |
| 7,368,481 B1 | 5/2008 | Rapisarda | |
| 2009/0004297 A1 | 1/2009 | Ranganathan | |

FOREIGN PATENT DOCUMENTS

EP 0208362 * 6/1986 ............. A61K 33/06

OTHER PUBLICATIONS

McGann et al. (BBA 1983, 760:415-420).*
Gaucheron, F. (Reprod Nutr Dev. 2005;45:473-483).*
Heaney, et al., "Absorbability and Cost Effectiveness in Calcium Supplementation," Journal of the American College of Nutrition, 2001, 20(3):239-246.
Nicar, et al., "Calcium bioavailability from calcium carbonate and calcium citrate," Journal of Clinical Endocrinology and Metabolism, 1985, 61(2):391-393.

* cited by examiner

*Primary Examiner* — Ernst V Arnold
(74) *Attorney, Agent, or Firm* — Yonggang Ji

(57) ABSTRACT

An oral dosage form for administration to an animal comprising a biologically utilizable form of calcium and an extended release system that maintains the calcium level in the animal's bloodstream at a substantially beneficial level for a defined period of time.

1 Claim, 2 Drawing Sheets

Average Plasma Calcium Levels in Dogs

CALCIUM SUPPLEMENT

BACKGROUND OF THE INVENTION

1. Field of the Invention

This invention relates to solid dosage forms comprising an extended release formulation of calcium salts and to methods for making and using the formulation.

2. Description of Related Art

Calcium is an important human dietary component required for bone formation and maintenance, as well as for many other metabolic functions including functions of the heart, muscles, and nervous system. Calcium from ordinary dietary sources, however, can be insufficient to assure that adequate calcium levels are available in the body to maintain these functions.

To combat this insufficiency, calcium compounds have long been used in the art in various forms, either alone or as ingredients in blends of nutritional supplements. These nutritional supplements include liquids, such as Ensure® brand liquid supplements, and solid dosage forms, such at tablets or capsules. These solid dosage forms may comprise only a calcium supplement, as found in some Citracal® brand calcium supplements or as one ingredient in a combination of supplements, such as in One-A-Day® brand multivitamins.

Calcium supplements have proven beneficial for many different age groups. Children can benefit from having calcium levels sufficient to facilitate bone growth, adults can benefit from calcium levels sufficient to maintain bone health, and seniors can benefit from calcium levels sufficient to minimize bone loss related to osteoporosis. Nutritional supplements containing calcium have even been described for cats (U.S. Pat. No. 7,368,481 to Rapisarda, issued May 6, 2008).

Osteoporosis can be made worse in seniors by an impaired production of vitamin D, which normally stimulates calcium absorption. As a result, calcium is not absorbed as efficiently from the intestines in some seniors. Metabolic processes that require calcium can then draw that calcium from bones, causing a loss in bone density (as described in U.S. Pat. No. 4,772,467 to Pak, issued Sep. 20, 1988). An increased level of calcium in the intestines increases the amount of calcium absorbed, which can help reduce or prevent the loss in bone density. Magnesium has also been proposed as an ingredient that can have beneficial effects if administered in conjunction with calcium.

One difficulty encountered with both solid and liquid forms of calcium supplements lies in the size of the dose. Some authorities have recommended daily levels of calcium as high as 1,000 to 1,500 mg/day. In addition to the calcium ion active ingredient, tablets or liquid suspensions or solutions may also contain an anion species for the calcium ions and various tablet ingredients such as fillers, excipients, lubricating agents, disintegrants, and other ingredients that are well-known in the art of making tablets. Solutions and suspensions also require a carrier fluid and may also include anti-foaming agents, preservatives, stabilizers, and other materials well known in the art of preparing medicinal solutions or suspensions. If a nutritional supplement is to provide that level of calcium, the amount of liquid or the size of the tablet or tablets can be daunting for a person to take in a single dose.

Another problem with large dosage levels of calcium lies in the limits of absorption of calcium by the body and the excretion pathways for calcium. The body can only absorb a limited amount of calcium at a time. Very high levels of available calcium can affect the ability of the stomach or intestine to absorb the calcium. When a large dose of calcium is administered all at once, much of the calcium cannot be absorbed at all. Likewise, the kidneys, which separate excess ions from the blood, tend to separate calcium ions from the blood more quickly when calcium blood levels are high. Once absorbed, the calcium can only be used by the body at a limited rate over the course of the day. Bone formation and maintenance, heart, muscle, and nervous system function and many other metabolic functions that require calcium do not occur at constant rates throughout the day or only in the morning. A single dose of calcium taken in the morning, for example, may not maintain the appropriate levels of calcium in the body throughout the day. Thus, much of the calcium that is administered in a large single dose may either not be absorbed or, if absorbed, may be removed by the kidneys before the body may put it to productive use.

The most direct approach to overcome the inability of the body to put large doses of calcium to use all at once is to administer multiple doses of calcium over the course of a day. Many over-the-counter supplements follow this approach. Caltrate® 600 supplement, for example, advises taking one 600 mg tablet twice daily with food, for a daily dose of 1,200 mg of calcium. One drawback of multiple daily administrations is compliance with the regimen. Particularly with over-the-counter supplements, consumers often forget to take a second or third dose.

Another approach is to employ extended release technology to regulate or delay absorption of the calcium supplement dose. Extended release technology includes delayed release technology and sustained release technologies, including controlled release technology and prolonged release technology.

Delayed release technologies incorporate separate amounts of an active ingredient dose into separate parts of a delivery system. The separate parts of the delivery system are designed to make their portion of the dose available at different times. An example of a delayed release technology would be a multi-layer tablet having separate film coats over each layer. As the tablet moves through the digestive tract, successive layers containing the active ingredient become available for dissolution and use. A graph showing the concentration of the active ingredient in the blood stream over time would be expected to show a series of spikes as each successive layer dissolves.

Sustained release technology uses slow release of active ingredients from a monolithic dosage form. A graph of the concentration of the active ingredient in the blood stream over time would be expected to be a smooth curve. The difference between controlled release technology and delayed release technology is that the concentration of the active ingredient must remain at or about a predefined level in the blood stream for a defined period of time, but in delayed release technology, the concentration of the active ingredient is not constrained to remain at predetermined level.

Various sustained release calcium formulations have been introduced into the market, but those in need of calcium supplements still require a consistent, reliable, single administration, daily dosage form that provides a full day's supply of calcium over an extended time.

SUMMARY OF THE INVENTION

The principal object of the invention therefore is to provide such a consistent, reliable, single administration daily dosage form for a full day's supply of calcium. The invention comprises a solid dosage form that delivers calcium ions to a consumer over the course of a fixed time period (preferably up to 24 hours) after ingestion to approximate the continuous delivery of calcium to the body.

Another object of the invention is to provide a method for treating a human in need of calcium supplementation using a solid dosage form that delivers calcium salts to a consumer over the course of a fixed time period (preferably 24 hours) after ingestion to approximate the optimized delivery regimen of calcium to the body.

An advantage of the invention is that the solid dosage form can be smaller than ordinary solid dosage forms containing calcium salts because greater absorption of the calcium in the course of a day means that more calcium provided by the dosage form is actually used by the body, and less useless calcium is eliminated.

Another advantage of the invention is that the solid dosage form may be taken only once per day, rather than twice per day as is the case with most calcium supplements.

Yet another advantage of the invention is that slowing the release of a single dose tablet of calcium decreases unpleasant side effects associated with taking calcium supplements such as bloating and gas, especially with carbonate and bicarbonate forms of calcium supplements.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides an oral dosage form for administration to an animal comprising a biologically utilizable form of calcium and an extended release system for releasing the biologically utilizable form of calcium over an extended period of time after administration of the dosage form to the animal, whereby the calcium level in the bloodstream is maintained at a substantially beneficial level substantially for a defined period of time. Preferably, the calcium is a salt selected from the well known over-the-counter calcium supplement salts, such as calcium carbonate, calcium citrate, calcium glutonate and calcium bicarbonate, and preferably, the extended release system comprising hydroxypropyl methylcellulose.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS OF THE INVENTION

Figure 1:
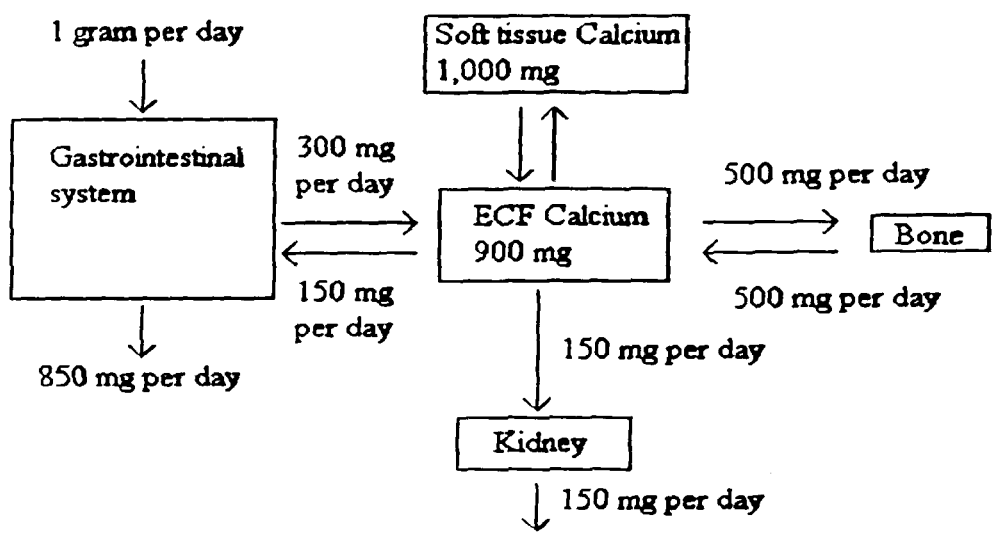
FIG. 1 shows a diagram of calcium transport and use in the body, along with the respective amounts of calcium transported per day among various systems of the body.

Reference will now be made in detail to the presently preferred embodiments of the invention.

The invention comprises an oral dosage form. An oral dosage form may comprise any known liquid form, such as a solution or a suspension, or any known solid form, such as coated or uncoated capsules, caplets, tablets, pills, buccal lozenges sachets, effervescent tablets and any other solid or liquid form known in the field. The composition of the invention may also be administered in other ways, such as injection or nasal sprays. But, since the main advantages of the invention are realized through daily administration, injections could be inconvenient and uncomfortable to administer. Also, to be effective to the fullest extent, the amount of calcium that should be administered should be sufficient for systemic benefits, and administration by nasal spray generally does not deliver the amounts required for systemic benefits in one or two squeezes of the container.

The invention may be administered to any animal in need of therapeutic calcium administration. The most preferable animal is a human being, but pets, farm animals and other animals that are of sufficient value to justify daily calcium administration are also preferred.

The formulation of the invention comprises a biologically utilizable form of calcium. Typically, biologically utilizable forms of calcium include calcium salts of biologically acceptable salts. These salts include edible calcium salts, such as acetate, ascorbate, oxide, phosphate, halide (especially chlorides), citrate, gluconate, carbonate, bicarbonate, lactate and gluceptate salts (although gluceptate salts are generally preferred for intravenous injection). Mixtures of salts may also be used. Binary or ternary mixtures of calcium carbonate, calcium bicarbonate and calcium citrate are preferred. A mixture of calcium carbonate and calcium citrate is more preferred and a mixture of about 75% by weight calcium carbonate and about 25% by weight calcium citrate is most preferred. References to "calcium" herein are, where appropriate, intended to encompass all such biologically acceptable salts as well as elemental or ionic calcium, as appropriate. The calcium may also be administered in conjunction with other active ingredients that either act independently of the calcium (such as multivitamin formulations) or that support or enhance the function of calcium, such as Vitamin D or Magnesium.

The invention also comprises an extended release system for releasing the calcium into the body of the animal over an extended period of time. Extended release technologies are well known in the art, and any biologically acceptable form of such system may be used. A sustained release system is preferred over a delayed release system, primarily for reasons of ease and expense of manufacture, and a controlled release system is most preferred, although a delayed release system may by used as well. Preferred systems include matrix systems, where the calcium is dispersed in a solid, inert matrix and the calcium becomes available for absorption by diffusion through this matrix. Acceptable matrix materials include plastics, hydrophilic polymers, and fatty compounds. Preferred materials include methyl acrylate and methyl methyacrylate polymers and copolymers, polyvinyl chloride, polyethylene, methylcellulose, hydroxypropyl methylcellulose, alkali carboxymethylcellulose (especially sodium carboxymethylcellulose), and waxes, such as carnauba wax and glyceryl tristearate. Hydrophilic polymers are preferred, and hydroxypropyl methylcellulose is highly preferred. Those skilled in the art will recognize that these ingredients may be combined in many ways to obtain a satisfactory extended release system. Other systems, such as osmotic systems or ion-exchange resins may be used, but these systems are not preferred because of cost and complexity considerations.

Various methods are known in the pharmaceutical industry for providing extended or extended release of pharmaceutical actives. These methods are, for the most part, based on associating the pharmaceutical material with another material that reacts differently to the acidic environment of the stomach and the more basic environment of the small intestine. These methods are intended to delay release of the pharmaceutical active and include, for example, incorporation of the pharmaceutical active in hydroxypropyl methylcellulose as described in U.S. Pat. No. 4,571,333 to Hsiao et al., issued Feb. 18, 1986. Other polymeric matrices are also known, such as those described in U.S. Pat. No. 6,090,411 to Pillay et al., issued Jul. 18, 2000, U.S. Pat. No. 5,965,163 to Miller et al., issued Oct. 12, 1999, and U.S. Pat. No. 4,784,858 to Ventouras, issued Nov. 15, 1988. These extended release materials may be combined with ordinary release materials to form compressed tablets that may be substantially uniform mixtures or layered tablets comprising the ordinary or immediate release material and the delayed release material. The compressed tablets made from these materials may be coated or uncoated. The coating materials may also be designed to delay release of the coated material.

These delayed release formulations are usually designed to release the pharmaceutical actives at a declining rate over time. Usually, the rate at which the active is released is directly dependent upon the amount of active material remaining in the tablet as it passes through the gastrointestinal system. Some patents purport to offer approaches that allow release profiles that are independent of the amount of remaining pharmaceutical active, such as U.S. Pat. No. 6,090,411 to Pillay et al., issued Jul. 18, 2000.

Another acceptable extended or delayed release technology is described in U.S. Pat. No. 5,811,126 to Krishnamurty, issued Sep. 22, 1998. This system uses a cross-linked sodium alginate, a water swellable polymer such as a cellulose ether, and an edible hydrocarbon derivative to form a matrix surrounding an active ingredient.

In addition, the solid dosage form may be coated or encapsulated. Coating materials are well known in the art, and the coating or encapsulation material may or may not contain calcium as appropriate for the use of the formulation.

In the invention, the calcium level in the bloodstream is maintained at a substantially beneficial level for a defined period of time. Preferably, in accordance with the invention, the calcium level in the human body should be maintained at from about 12 milligrams of calcium per deciliter of blood (mg/dL) to about 15 mg/dL, more preferably, from about 24 mg/dL to about 20 mg/dL, even more preferably from about 17 mg/dL to about 19 mg/dL, and most preferably about 18 mg calcium per deciliter of blood (mg/dL). These values can be approximately transcribed to total milligrams in the blood by recognizing that the average human body contains about 5 liters of blood. The conversion is X mg/dL multiplied by 10 deciliters per liter multiplied by an average 5 liters of blood in the human body. Accordingly, the normal calcium level in the adult human body is from about 9.0 mg/dL to about 10.5 mg/dL or about 450 mg to about 525 mg (measured as total milligrams in the bloodstream). To increase bone density, should be maintained at from about 600 mg to about 1,200 mg, more preferably from about 800 mg to about 1,000 mg, even more preferably from about 850 mg to about 950 mg, and most preferably about 900 total mg of calcium in the blood. Those skilled in the art will recognize that the actual number of milligrams in the blood will depend on the dosage given and the total amount of blood in the body of the person consuming the dose. Thus, one skilled in the art will appreciate that the milligram amounts provided herein may be adjusted for the size of the person consuming the supplement and the many factors that can affect calcium metabolism in a human body.

The oral dosage form should provide controlled levels of calcium to a consumer of the dosage form for extended period of time. Many active ingredients are only found in the blood stream for about four hours after initial administration. An extended period of time should be at least about six hours, more preferably eight hours, and even more preferably more than ten hours. Most dosage regimens require daily doses, taken in the morning or the evening. Twelve and even twenty-four hour extended periods are thus the most preferred times.

Formulations comprising hydroxypropylmethycellulose (HPMC) slow the release of elemental calcium in buffered solutions. In addition, such formulations have shown significantly greater absorption versus currently marketed calcium supplements, such as OsCal® and Caltrate® supplements. Formulations containing preferred calcium salts and HPMC showed higher net amount of total calcium absorbed by the body after oral administration of formulations having the equivalent of 1200 mg of elemental Ca. The formulations also released less gas from hydration of the carbonate anions immediately upon ingestion. Therefore, less bloating and gas were observed than would be the case with calcium carbonate and bicarbonate salts. Correspondingly, the formulations showed reduced amounts of unused calcium eliminated by the body, which means that a smaller daily dose of calcium is required to achieve a satisfactory steady state calcium balance in the body. In accordance with the invention, this steady state calcium level is maintained throughout the day by the continuous release of calcium from the administered dosage form. Current commercial calcium products that require administration two or more times a day show peaks and valleys of calcium levels above and below ideal levels.

Adequate dietary calcium must be absorbed from the digestive tract before it may be utilized by the body. The efficiency of calcium absorption is determined by several factors, including the physiological status of the person receiving the supplement and the particular chemical form of ingested calcium. Calcium bioavailability, or the amount of calcium available for intestinal absorption, may also vary among different calcium preparations (Nicar and Pak (1985) J. Clin. Endocrin. & Metab). V. 61, pp. 391-393).

Absorption of calcium in the average human body is shown in the diagram of FIG. 1, 900 milligrams (mg) resides in blood serum. Approximately 500 mg of calcium may be exchanged between bone and the blood serum over a period of twenty-four hours. More specifically, the bone calcium enters the extra-cellular fluid ("ECF"), which includes blood serum, and calcium from extra-cellular fluids may then enter the blood serum. Those skilled in the art will recognize that the diagram of FIG. 1 does not distinguish between ECF and blood serum because the equilibrium between within the ECF allows the amount of calcium in the ECF and blood serum to remain fairly constant. If, however, calcium is needed for biological functions (identified as "soft tissue calcium in FIG. 1), and the ECF calcium is not sufficient to meet that need, calcium may be drawn from bone tissue through one or more biological processes. When there is excess calcium in the ECF, it can be absorbed by bone tissue.

About one gram of calcium enters the body per day in a normal diet. Of this amount, about 300 mg is absorbed by digestion, while 150 mg can find its way from ECF back to the gastrointestinal system. As a result, about 850 mg of calcium leaves the body in feces. The kidney also extracts a net amount of about 150 mg per day from the blood. Thus, in a normally functioning body, the calcium level remains substantially constant, in the absence of a calcium supplement. Thus, bone serves as an important storage point for calcium, and it contains about 99% of the total body calcium. If insufficient calcium is included in the diet, or if more calcium is required than normal for biological functions, calcium reserves in bone may be depleted.

Since the body is only able to absorb calcium in relatively small amounts, extended release of a calcium supplement can greatly increase the total amount of calcium absorbed by the body in twenty-four hours.

In a preferred embodiment of the invention, tablets containing calcium carbonate and calcium citrate and Vitamin D may be prepared having the formulation set forth in Table 1:

TABLE 1

Formulation of a Preferred Embodiment of the Invention

| Ingredient | Mg per tablet |
| --- | --- |
| Calcium Carbonate | 1,322.3 |
| Calcium Citrate | 437.9 |
| Magnesium Hydroxide | 110.4 |
| Hypromellose | 67.5 |
| Croscarmellose Sodium | 40.6 |
| Magnesium Silicate | 6.5 |
| Titanium Dioxide | 4.3 |
| Propylene Glycol/Dicaprylate/Dicaprate | 4.3 |
| Magnesium Stearate | 1.25 |
| Inulin, Oligofructose Enriched | 1.1 |
| Vitamin D3 | 0.018 |
| Total tablet weight (milligrams) | 1,996.168 |

Many of the ingredients set forth in Table 1 will be recognized by one skilled in the art as being conventional tablet ingredients. Calcium carbonate and calcium citrate provide the calcium in the calcium supplement of the invention, and magnesium hydroxide and vitamin D3 work with the calcium to provide additional benefits upon ingestion. Hypromellose is hydroxypropyl methylcellulose that acts as a rate controlling polymer for the sustained release aspect of the invention, and croscarmellose sodium is a cross-linked sodium carboxymethicelluose that is used as a disintegrant to help the compressed tablet dissolve. Titanium dioxide is a coating agent, as is Propylene glycol/dicapyriate/dicaprate. Magnesium stearate is a tablet lubricant, and Inulin is a source of fiber.

The preferred embodiment of the invention may also comprise various incidental excipients that are found as impurities in commercial raw materials or that are incorporated from various other sources. These incidental impurities include: acacia, sodium lauryl sulfate, DL-alpha Tocopherol, partially hydrogenated soybean oil, hydrolyzed bovine gelatin, sucrose, and corn starch.

Tablets comprising the formulation of Table 1 may be administered as two tablets per serving to deliver 1,200 mg of calcium in each serving. Two tablets is the preferred dosage, but a single tablet may also be used, for example in a chewable formulation where tablet size is not as critical as for a tablet that is swallowed whole. Multiple tablets may also be used.

All of the ingredients are typically available in powdered forms. Tablets of the preferred embodiment may be prepared as follows: (a) Calcium carbonate and vitamin D3 may be combined in a ribbon mixer to form a first premix; (b) magnesium hydroxide and calcium carbonate are blended in a V-blender, hypromellose, croscarmellose, and calcium citrate, are then added to the V-blender, followed by magnesium stearate. The remaining ingredients are then added to the mixture of powders; the blends are combined and then pressed into tablets.

The invention will be further illustrated by the following examples.

EXAMPLES 1-2

Tablets having the ingredients set forth in Table 2 were prepared to be compared to two commercial formulations. Methocel® K100 Premium LV CR and Methocel® K100M Premium CR are forms of hydroxypropyl methylcellulose (also know as hypermellose) available from Dow Wolf Cellulosics. Methocel® K100 Premium LV CR is reported to have an apparent viscosity (2% in water, 20° C.,) from about 80 cP to about 120 cP. Methocel® K100M Premium CR is reported to have an apparent viscosity (2% in water, 20° C.) from about 80,000 cP to about 120,000 cP.

TABLE 2

Formulations of Examples 1 and 2 in Weight Percent

| Ingredient | Example 1 | Example 2 |
| --- | --- | --- |
| Calcium Carbonate | 64.13% | 64.13% |
| Calcium Citrate Tetrahydrate | 21.66% | 21.66% |
| Magnesium Oxide | 3.46% | 3.46% |
| Vitamin D3 | 0.25% | 0.25% |
| Croscarmellose Sodium | 5.00% | 5.00% |
| Methocel K100 Premium LV CR | 2.50% | 2.00% |
| Methocel K100M Premium CR | 2.50% | 3.00% |
| Magnesium Stearate | 0.50% | 0.50% |
| Total | 100.00% | 100.00% |
| Ratio of Calcium Carbonate to Calcium Citrate | 75:25 | 75:25 |

Figure 2:
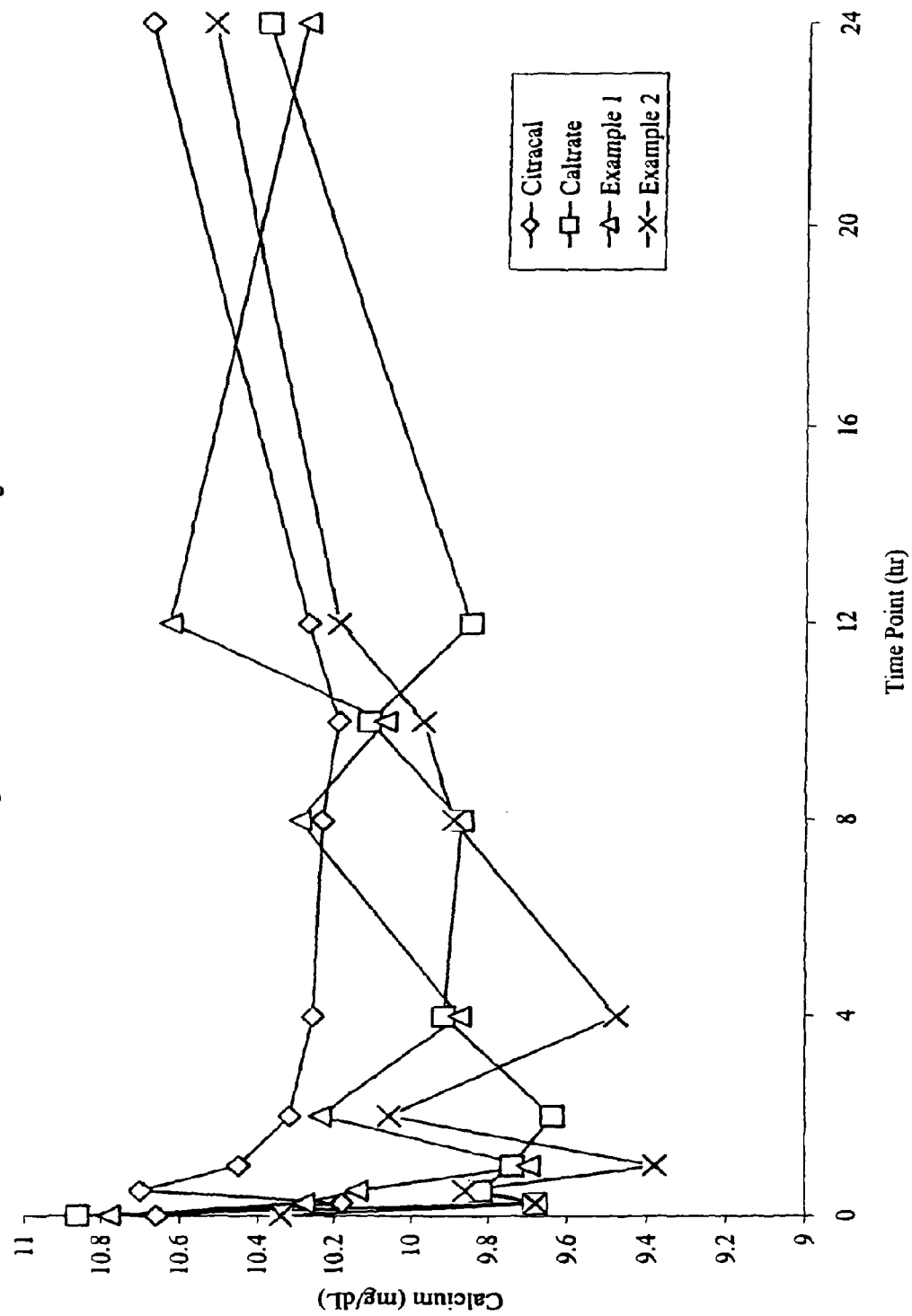
FIG. 2 shows total calcium plasma levels in dogs in a 24 hour test of two commercial formulations administered in accordance with recommended twice daily doses compared to single daily dose administration of two formulations of the invention.

A test was carried out on beagles using (a) the formulation of Example 1, (b) the formulation of Example 2, (c) a Citracal® plus Vitamin D tablet, and (d) half of a Caltrate® plus Vitamin D tablet. The test comprised three arms, with five dogs per arm. Each dog was fed the equivalent of 300 mg calcium, except that the formulations of Examples 1 and 2 were administered once a day and the commercial products were administered twice a day, in accordance with the label instructions for those products. Blood samples were taken over the course of 24 hours to determine the amount of calcium in the bloodstream. The results, measured in milligrams per deciliter, are shown Table 3 and in FIG. 2. The absolute blood concentration of each example is not as important as the comparison to the values of the other examples. The absolute levels of calcium in the beagles of the examples do not necessarily correspond to the levels that would be found in humans.

TABLE 3

| | Plasma Levels of Calcium in Dogs (mg/dl) | | | | | | | | | |
|---|---|---|---|---|---|---|---|---|---|---|
| Hours | 0 | 0.25 | 0.5 | 1 | 2 | 4 | 8 | 10 | 12 | 24 |
| | Calcium levels (mg/dl) | | | | | | | | | |
| Citracal | 10.66 | 10.18 | 10.7 | 10.45 | 10.32 | 10.26 | 10.24 | 10.2 | 10.28 | 10.7 |
| Caltrate | 10.86 | 9.68 | 9.82 | 9.74 | 9.64 | 9.92 | 9.88 | 10.12 | 9.86 | 10.4 |
| Example 1 | 10.78 | 10.28 | 10.14 | 9.7 | 10.24 | 9.88 | 10.3 | 10.08 | 10.64 | 10.3 |
| Example 2 | 10.34 | 9.68 | 9.86 | 9.38 | 10.06 | 9.48 | 9.9 | 9.98 | 10.2 | 10.54 |

The results demonstrate that the formulations of the invention were able to maintain the serum levels of calcium in dogs in the range of from about 9 mg/dL to about 11 mg/dL for the entire 24 hour period of the test. As a result, the calcium of Examples 1 and 2 was available for biological functions and storage in bones for an extended period of time, which allowed a large calcium dose to be absorbed and processed without the rapid elimination of excess calcium by the kidneys found when conventional calcium supplements make the entire dose of calcium available directly upon ingestion and without the necessity of twice daily administration.

The purpose of the above description is to illustrate some embodiments of the present invention without implying a limitation. It will apparent to those skilled in the art that various modifications and variations may be made in the apparatus or procedure of the invention without departing from the scope or spirit of the invention.

What is claimed is:

1. An oral dosage form for administration to an animal comprising a biologically utilizable form of calcium and a continuous release system for releasing said biologically utilizable form of calcium over an extended period of time after administration of said dosage form to said animal, wherein the formulation consisting essentially of
   1,322.3 mg of Calcium Carbonate;
   437.9 mg of Calcium Citrate;
   110.4 mg of Magnesium Hydroxide;
   67.5 mg of Hypromellose:
   40.6 mg of Croscarmellose Sodium;
   6.5 mg of Magnesium Silicate;
   4.3 mg of Titanium Dioxide;
   4.3 mg of Propylene Glycol/Dicaprylate/Dicaprate;
   1.25 mg of Magnesium Sterate;
   1.1 mg of Oligofructose Enriched Inulin; and
   0.018 mg of Vitamin D3;
and wherein the oral dosage form is adapted to maintain a steady state calcium level in the plasma of the animal by the continuous release of calcium from the administered dosage form for 24 hours.

* * * * *